United States Patent [19]

Heiss

[11] Patent Number: 4,508,903
[45] Date of Patent: Apr. 2, 1985

[54] PROCESS FOR THE PREPARATION OF 4,4'-BIS[BENZ(OX, OTHI OR IMID)AZOL-2-YL]STILBENES

[75] Inventor: Lorenz Heiss, Hofheim am Taunus, Fed. Rep. of Germany

[73] Assignee: Hoechst Aktiengesellschaft, Fed. Rep. of Germany

[21] Appl. No.: 488,090

[22] Filed: Apr. 25, 1983

[30] Foreign Application Priority Data

May 5, 1982 [DE] Fed. Rep. of Germany ....... 3216723

[51] Int. Cl.³ .................. C07D 413/10; C07D 417/10
[52] U.S. Cl. .................................. 548/156; 548/219; 548/175; 548/328
[58] Field of Search ................ 548/175, 219, 156, 328

[56] References Cited

U.S. PATENT DOCUMENTS

| 3,260,715 | 7/1966 | Saunders | 548/319 |
| 3,322,680 | 5/1967 | Hedberg et al. | 252/301.24 |
| 3,501,490 | 3/1970 | Maeder | 548/159 |
| 3,565,890 | 2/1971 | Tanaka | 548/159 |
| 3,586,673 | 6/1971 | Bloom et al. | 548/156 |
| 3,641,044 | 2/1972 | Matter | 548/219 |

FOREIGN PATENT DOCUMENTS 2333378  1/1975  Fed. Rep. of Germany ...... 546/156

OTHER PUBLICATIONS

Elderfield, Ed., vol. 5, Heterocyclic Compounds, Wiley, N.Y., N.Y., (1957), p. 507.
Khim. Geterotsikl. Soedinenii, 1981, 17:463-467, (Vernigor et al.).

Primary Examiner—Glennon H. Hollrah
Assistant Examiner—D. B. Springer
Attorney, Agent, or Firm—Connolly and Hutz

[57] ABSTRACT

A process for the preparation of 4,4'-bis[benz(ox, othi or imid)azol-2-yl]stilbenes of the formula

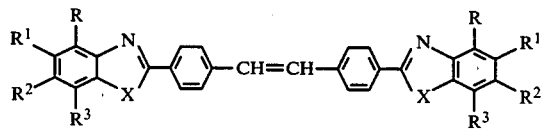

in which R, $R^1$, $R^2$ and $R^3$ are identical or different and denote hydrogen, $C_1$–$C_4$-alkyl, $C_1$–$C_4$-alkoxy, $C_1$–$C_4$-alkoxycarbonyl, chlorine, bromine, nitro or sulfo and X denotes oxygen, sulfur or NH, by reacting alkyl (4-halomethyl)iminobenzoates of the formula

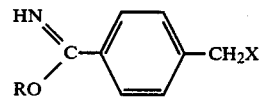

or their HCl or HBr salts, R denoting $C_1$–$C_4$-alkyl or $C_1$–$C_4$-alkoxyethyl and X denoting Cl or Br, with o-aminophenol, o-aminothiophenol or o-phenylenediamine and allowing the 2-benz(ox, othi or imid)azol-4-ylhalomethylbenzenes obtained thereby to react with an approximately equivalent amount of sodium tert.-butylate. The stilbene compounds obtained thereby are used as optical brighteners.

3 Claims, No Drawings

PROCESS FOR THE PREPARATION OF 4,4'-BIS[BENZ(OX, OTHI OR IMID)AZOL-2-YL]STILBENES

A process for the preparation of bis(benzoxazolyl)-stilbenes is already known from Khim. Geterozikl. Soedin. 1981, pages 463–467, in which 2-benzoxazolyl(4-bromomethyl)benzene is dehydrobrominated with potassium tertiary-butylate. The particular disadvantage of this process is the fact that it involves the necessity for an approximately four- to eight-fold excess of costly potassium tertiary-butylate.

An improved process for the preparation of 4,4'-bis[benz(ox, othi, or imid)azol-2-yl]stilbenes of the formula

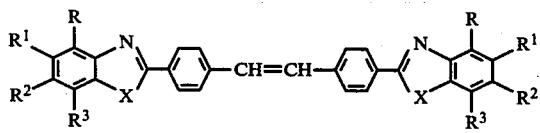

has now been found, in which R, $R^1$, $R^2$ and $R^3$ are identical or different and denote hydrogen, $C_1$–$C_4$-alkyl, $C_1$–$C_4$-alkoxy, $C_1$–$C_4$-alkoxycarbonyl, chlorine, bromine, nitro or sulfo and X denotes oxygen, sulfur or NH, which comprises reacting alkyl (4-halomethyl)iminobenzoates of the formula

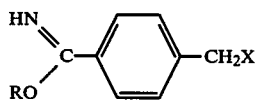

or their HCl or HBr salts, R denoting $C_1$–$C_4$-alkyl or $C_1$–$C_4$-alkoxyethyl and X denoting Cl or Br, with o-aminophenol, o-aminothiophenol or o-phenylenediamine and allowing the 2-benz(ox, othi, or imid)azolyl-4-halomethylbenzenes obtained thereby to react with an approximately equivalent amount of sodium tert.-butylate.

The alkyl (4-halomethyl)iminobenzoates serving as starting compounds are prepared by dispersing p-cyanobenzyl chloride or p-cyanobenzyl bromide in an excess of the alcohol of the formula R-OH and passing in hydrogen chloride or bromide. By this means, the HCL or HBr salts of the iminoesters of the formula given above are obtained.

These salts are then reacted with an o-aminophenol, o-aminothiophenol or o-phenylenediamine by heating in an inert organic solvent, preferably in a lower alcohol, at temperatures from room temperature to the boiling point of the solvent.

It has been found that the yields in this reaction can be considerably increased if it is carried out with an excess of weak anhydrous acids, preferably acetic acid, in order to prevent the side reaction, an alkylation by the chloromethyl group. This finding is surprising, since a drastic decrease in the yields is obtained with an excess of a strong acid. It is also possible to prepare 2-benzoxazolyl-4-halomethylbenzene directly from p-cyanobenzyl chloride or p-cyanobenzyl bromide without intermediate isolation of the iminoester in the following manner. Initially, p-cyanobenzyl chloride or p-cyanobenzyl bromide is dispersed in an excess of the alcohol of the formula R-OH, hydrogen chloride or bromide is passed in and the reaction is allowed to continue for some hours until the nitrile band at 2,220 $cm^{-1}$ in the infrared spectrum has disappeared. The excess of hydrogen halide is then neutralized with a base, preferably with sodium carbonate, and the reaction mixture is again acidified by the addition of a weak acid, preferably acetic acid. Then o-aminophenol, o-aminothiophenol or o-phenylenediamine is added and the mixture is heated to temperatures from 30° to 80° C. After completion of reaction, water is added, and the reaction product is filtered off with suction and washed with water. By this means, the 2-benzoxazolyl-4-halomethylbenzene or the corresponding benzothiazolyl or benzimidazolyl compounds are obtained.

In order to prepare the stilbene compounds, these halomethylbenzene compounds are dissolved in an aprotic polar solvent and dehydrohalogenated by the addition of approximately an equivalent amount of sodium tert.-butylate. The preferred solvent is dimethylformamide. The reaction temperature is about 10° to 50° C. The reaction is preferably carried out in such a manner that initially the sodium tert.-butylate is produced in situ in the solvent from sodium hydride and tert.-butanol. The halomethylbenzene compound is then added to this dispersion. To work up, water is initially added to the reaction mixture and it is made slightly acid with mineral acid. The stilbene compound is then conventionally filtered off, washed and dried. These stilbene compounds are obtained analytically pure in quantitative yield.

The advantage of this dehydrohalgenation in dimethylformamide with sodium tert.-butylate compared with the process described in Khim. Geterozikl. Soedin 1981, pages 463–467, is that in this case, surprisingly, a quantitative yield is obtained with the equivalent amount of sodium tert.-butylate, while the yields are lower in the previously known process in spite of using a four- to eight-fold excess of potassium tert.-butylate. Moreover, it was surprising that synthesis in dimethylformamide provides significantly purer products than in dimethyl sulfoxide as was the fact that the halomethylbenzenes are significantly more soluble in dimethylformamide than in dimethyl sulfoxide. This gives rise to an improvement in the space-time yield.

The stilbene compounds of the formula 1 are used as optical brighteners.

EXAMPLE 110 g (0.5 mole) of methyl p-chloromethyliminobenzoate hydrochloride and 54 g (0.5 mole) of o-aminophenol are dissolved in 800 ml of methanol and stirred at 65° C. for about 1 hour. The solution of the ammonium chloride formed is then cooled down to room temperature, about 500 ml of water are added and the mixture is filtered with suction. The benzoxazolyl-2-(4-chloromethyl)-benzene is washed with water and, after drying, 110 g (90.5% of theory) are obtained. Melting point: 150°–151° C.

found: C=69.0%, H=4.1%, N=5.7%, Cl=14.5%, calculated: C=69.1%, H=4.1%, N=5.8%, Cl=14.6%.

3.6 g of tertiary-butanol and 1.6 g of sodium hydride (80% pure) are dispersed in 150 ml of dimethylformamide under an atmosphere of nitrogen and stirred for one hour, then, cooling to 20° C., 9.8 g (0.04 mole) of benzoxazolyl-2-(4-chloromethyl)benzene are added and the mixture is stirred at 20° C. for six hours. It is then diluted with 100 ml of water and the pH is adjusted to 5–6 with hydrochloric acid. After filtration with suction, the product is thoroughly washed with water and methanol and dried. 4,4'-Bis(benzoxazol-2-yl)stilbene is obtained as greenish crystals in a yield of 8.1 g (97.8%).
Melting point: 355°–360° C.

found: C 80.6%, H 4.3%, N 6.8%, calculated: C 81.1%, H 4.3%, N 6.8%.

In the same manner, initially the 4-halomethylbenzenes listed in the following table were prepared, from which the stilbene compounds listed in Table 2 were then obtained.

TABLE 1

| Example | Starting materials | Final products | Melting Point | Analysis for C, H, Cl | Yield |
|---------|-------------------|----------------|---------------|-----------------------|-------|
| 2 | CH₃-C₆H₃(NH₂)(OH) | CH₃-benzoxazole-C₆H₄-CH₂Cl | 144° C. | found 69.7%; 4.8%; 13.5% calc. 69.9%; 4.7%; 13.8% | 91% |
| 3 | O₂N-C₆H₃(NH₂)(OH) | O₂N-benzoxazole-C₆H₄-CH₂Cl | 138° C. | found 58.1%; 3.3%; 11.9% calc. 58.2%; 3.1%; 12.2% | 88% |
| 4 | C₂H₅O-CO-C₆H₃(NH)(OH) | C₂H₅O-CO-benzoxazole-C₆H₄-CH₂Cl | 137° C. | found 64.6%; 4.4%; 11.0% calc. 64.8%; 4.4%; 11.3% | 82% |
| 5 | Cl-C₆H₃(NH₂)(OH) | Cl-benzoxazole-C₆H₄-CH₂Cl | 167° C. | found 60.0%; 3.3%; 24.9% calc. 60.3%; 3.2%; 25.5% | 86% |
| 6 | C₆H₄(NH₂)₂ | benzimidazole-C₆H₄-CH₂Cl | sublimed 200° C. | found 68.9%; 4.8%; 14.2% calc. 69.2%; 4.6%; 14.6% | 90% |
| 7 | C₆H₄(NH₂)(SH) | benzothiazole-C₆H₄-CH₂Cl | 114° C. | found 64.3%; 3.8%; 13.5% calc. 64.9%; 3.9%; 13.7% | 56% |
| 8 | NaO₃S-C₆H₃(NH₂)(OH) | NaO₃S-benzoxazole-C₆H₄-CH₂Cl | — | found 48.3%; 2.7%; 10.2% calc. 48.7%; 2.6%; 10.2% | 51% |

TABLE 2
| Example | Starting materials | Final products | Melting point | Analysis for C, H, N | Yield |
|---|---|---|---|---|---|
| 2 |  | 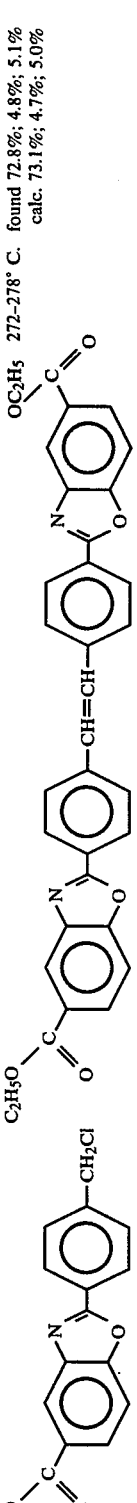 | 280–285° C. | found 80.8%; 5.1%; 6.2%<br>calc. 81.2%; 5.2%; 6.3% | 94% |
| 3 |  | 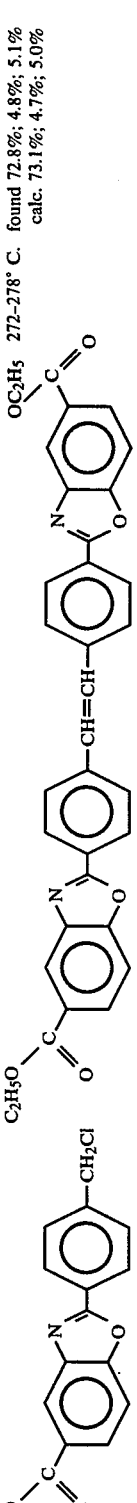 | 272–278° C. | found 72.8%; 4.8%; 5.1%<br>calc. 73.1%; 4.7%; 5.0% | 88% |
| 4 |  | 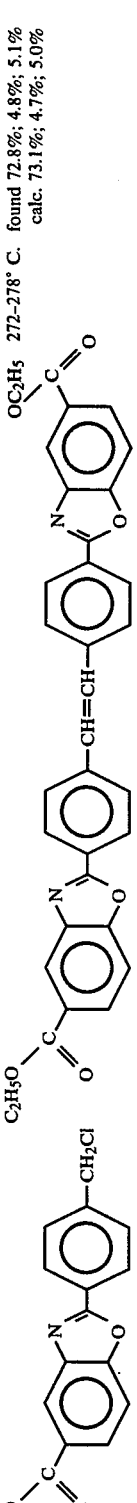 | 306–310° C. | found 69.1%; 3.3%; 5.7%<br>calc. 69.6%; 3.3%; 5.8% | 91% |
| 5 |  | 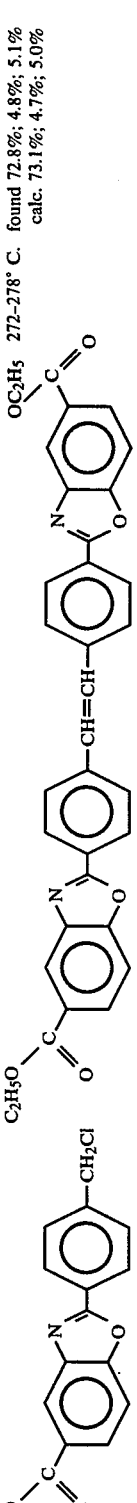 | >340° C. decomposition | found 81.2%; 4.7%; 13.5%<br>calc. 81.6%; 4.8%; 13.6% | 86% |
| 6 |  | 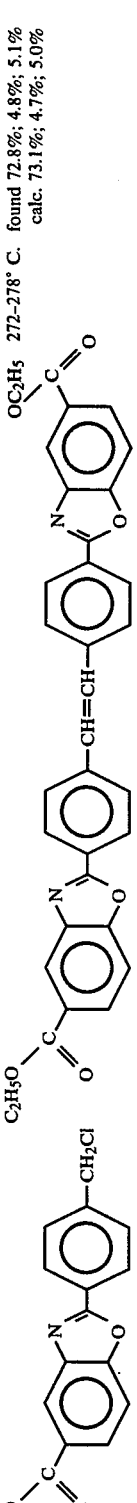 | 302–308° C. | found 75.0%; 4.1%; 3.1%<br>calc. 75.3%; 4.0%; 3.1% | 72% |
| 7 |  | 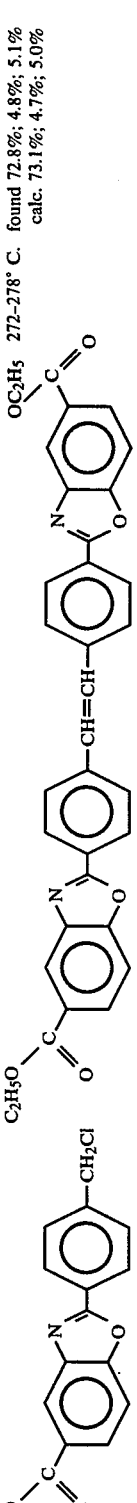 | >360° C. | found 53.9%; 2.5%; 4.4%<br>calc. 54.4%; 2.6%; 4.5% | 76% |
| 8 |  | 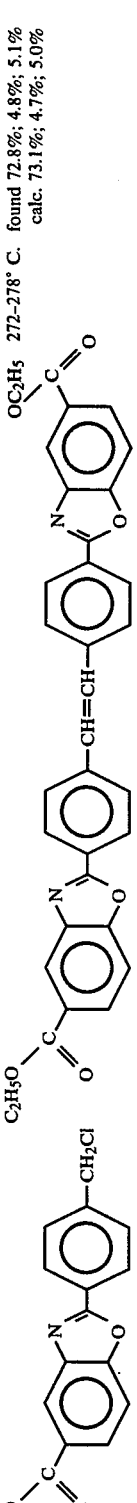 | 358–362° C. | found 80.7%; 4.3%; 6.7%<br>calc. 81.1%; 4.3%; 6.8% | 90% |

I claim:

1. A process for the preparation of a 4,4'-bis[benz(ox, othi or imid)azol-2-yl]stilbene of the formula

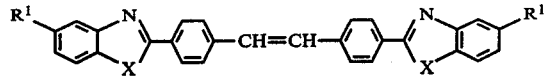

in which the $R^1$ groups are identical or different and denote hydrogen, $C_1$–$C_4$-alkyl, $C_1$–$C_4$-alkoxy, $C_1$–$C_4$-alkoxycarbonyl, chlorine, bromine, nitro or sulfo and X denotes oxygen, sulfur or NH, which comprises reacting an alkyl (4-halomethyl)iminobenzoate of the formula

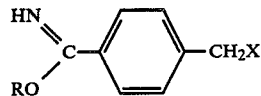

or its HCl or HBr salts, R denoting $C_1$–$C_4$-alkyl or $C_1$–$C_4$-alkoxyethyl and X denoting Cl or Br, with o-aminophenol, o-aminothiophenol or o-phenylenediamine and allowing the 2-benz(ox, othi or imid)azol-4-ylhalomethylbenzene obtained thereby to react with an approximately equivalent amount of sodium tert.-butylate.

2. The process as claimed in claim 1, wherein the 2-benz(ox, othi or imid)azol-4-ylhalomethylbenzenes are allowed to react with an approximately equivalent amount of sodium tert.-butylate in dimethylformamide.

3. The process as claimed in claim 1, wherein the sodium tert.-butylate is produced in situ from sodium hydride and butanol.

* * * * *